United States Patent [19]

Rathbone et al.

[11] Patent Number: 4,617,269
[45] Date of Patent: Oct. 14, 1986

[54] PROCESS FOR THE PREPARATION OF FRUCTOSYL DISACCHARIDES

[75] Inventors: Elner B. Rathbone, Wokingham; Andrew J. Hacking; Peter S. J. Cheetham, both of Reading, all of England

[73] Assignee: Tate & Lyle Public Limited Company, England

[21] Appl. No.: 622,853

[22] Filed: Jun. 21, 1984

[30] Foreign Application Priority Data

Jun. 21, 1983 [GB] United Kingdom ............... 8316790

[51] Int. Cl.$^4$ ..................... C12P 19/18; C12N 9/10; C12R 1/125
[52] U.S. Cl. ..................... 435/97; 435/193; 435/839
[58] Field of Search .................. 435/193, 97

[56] References Cited

U.S. PATENT DOCUMENTS 4,309,505  1/1982  Smith et al. .................. 435/193
4,380,476  4/1983  Mufti et al. .................. 127/46.3

FOREIGN PATENT DOCUMENTS 166981   10/1982  Japan ......................... 435/193
2046757A 11/1980  United Kingdom .

OTHER PUBLICATIONS.

Dedonder, Methods in Enzymology, vol. 8, pp. 500–505 (1966).

Primary Examiner—Lionel M. Shapiro
Attorney, Agent, or Firm—Ostrolenk, Faber, Gerb & Soffen

[57] ABSTRACT

A process for preparing a fructoside, especially a fructosyl disaccharide, comprises reacting a fructosyl saccharide such as sucrose or raffinose with an alcohol or aldose in the presence of a fructosyl-transferase, especially one derived from B. subtilis NCIB 11811, 11872 or 11873. In particular, aldose is a compound of the formula

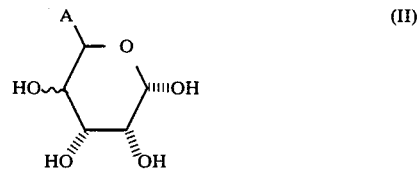

(II)

in which A represents a hydrogen atom or the group $CH_2X$, where X represents a hydrogen atom or an alkoxy group, and the fructosyl disaccharide so formed is halogenated to provide a halosucrose or halogalactosucrose sweetener.

17 Claims, No Drawings

PROCESS FOR THE PREPARATION OF FRUCTOSYL DISACCHARIDES

This invention relates to the preparation of fructosyl disaccharides, and especially halosucrose sweeteners, in particular 4,1′,6′-trichloro-4,1′,6′-trideoxy-galactosucrose (known as TGS), by means of an enzymatic reaction.

4,1′,6′-trichloro 4,1′,6′-trideoxy-galactosucrose is a potent sweetener described and claimed with other chlorosucrose derivatives in U.K. Pat. No. 1543167. Analogues in which the 6-hydroxy group is etherified or missing are disclosed in EP No. 0103479A and GB No. 2127806A. Analogues containing other halo substituents are disclosed in GB No. 2104063A. One method of preparation of TGS is described and claimed in GB No. 2079749A and U.S. Pat. No. 4,380,476. This method involves the preparation of a 6-ester of sucrose, or a mixture containing predominantly the 6-ester of sucrose, and then selectively chlorinating this 6-substituted material. Subsequent deesterification at the 6-position yields TGS. In practice, it is difficult to obtain a sucrose 6-ester in good yield in a specific manner when using chemical means. We have now found that preparation of TGS from a 6-substituted sucrose derivative can be achieved without difficulty by using an enzyme-based reaction starting from the corresponding 6-substituted glucose and a fructoside sugar, to produce a 6-substituted sucrose free from any other sucrose derivatives substituted at other positions, and easily separable from starting materials and glucose.

The enzyme in question is a fructosyltransferase. Fructosyltransferases are well known in enzymology. A representative enzyme is the so-called levansucrase, responsible for the production of levan, a polyfructose derivative, in the decomposition of sucrose or of raffinose. In its normal mode of action, levansucrase splits the glucose-fructose link in sucrose and transfers the fructose to an acceptor sugar, e.g. sucrose itself. This process is repeated so that fructose chains are built up. If another sugar is present besides sucrose, e.g. D-xylose, the levan formation is inhibited, or at least reduced, and instead the fructose is transferred to the other competing sugar which acts as an acceptor to produce a new fructoside. The new fructoside will also act as a donor, so in practice a large excess of donor has been used in order to push the equilibrium in the desired direction.

Hestrin and Avigad, in Biochem.J.69(1958) 388–398, showed that a range of sugars acted as good fructose-acceptors and thus tended to inhibit levan formation; others were poor acceptors; while a third class were apparently inert and failed to inhibit levan formation. In the last category was D-glucose 6-phosphate. All the other sugars referred to in the paper were sugars which were underivatised. However, the reaction of glucose 6-phosphate with sucrose in the presence of an enzyme derived from a mutant of Bacillus subtilis Marburg strain 168 is described in Kunst et al in Eur.J.Biochem. 42, 611–620 (1974). These, and other authors (e.g. Dedonder, Methods Enzymol., 8, 500–505) always used a high ratio of fructose donor (e.g. sucrose) to acceptor, e.g. from 5:1 to 10:1, and a low concentration which would not be practicable on an industrial scale. A similar reaction is described in U.K. Patent Application No. 2046757A where a variety of aldose starting materials are reacted with sucrose or raffinose in the presence of a levansucrase derived from a range of microorganisms including Actinomyces viscosus and B.subtilis (Strain ATCC 6051, i.e. the Marburg strain). In the patent application, however, the aldose is always an underivatised sugar and the mole ratio of donor to acceptor used is 1:5, presumably in order to minimise chain-forming reactions.

We have now found that 6-derivatised sucrose derivatives can be prepared by reacting the corresponding 6-derivatised glucose or galactose with a fructosyl transferase in the presence of sucrose or raffinose or stachyose. The product can then be halogenated in the 4,1′ and 6′-positions and, if desired, the 6-derivatising group removed to yield the required halosugar. The initial reaction proceeds in good yield in the absence of the production of any levan.

According to the present invention we provide a process for the preparation of a halodeoxy sucrose or galactosucrose derivative of the general formula

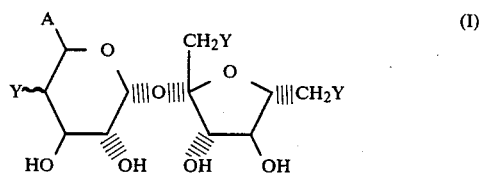

(I)

in which A represents a hydrogen atom or the group CH$_2$X, where X represents a hydrogen atom, or a hydroxy or alkoxy group and Y represents a halogen atom, comprising reaction of an aldose of the general formula

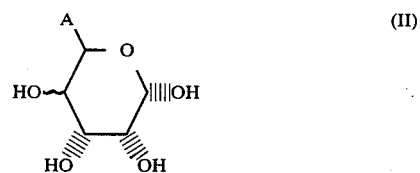

(II)

in which A represents a hydrogen atom or the group CH$_2$X, where X represents a hydrogen atom or an alkoxy group or a protected hydroxy group, with a fructosyl di or oligo-saccharide in the presence of a fructosyltransferase to obtain a compound of the general formula

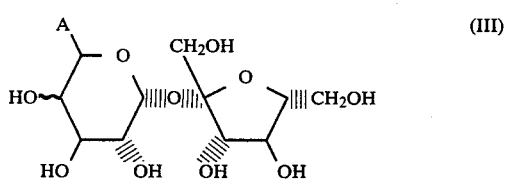

(III)

in which A is as defined for formula II; separating the compound of formula III; halogenating the compound of formula III and, for a compound of the formula I in which A represents CH$_2$X and X represents a hydroxy group, de-protecting the protected hydroxy group.

The fructosyltransferase used in the reaction according to the present invention is preferably derived from B.subtilis or Erwinia sp. (previously known as Aerobacter levanicum). B.subtilis is a particularly preferred source since strains are very easy to grow on a large scale in conventional fermentations and they are well accepted as sources of industrial enzymes (e.g. α-amylases and β-lactamases). Furthermore, the fructosyltransferase is a predominantly exocellular enzyme and can thus be obtained and purified more easily. It is important that the enzyme used should be free of invertase activity. If necessary, a selective invertase-inhibitor must be used, such as p-hydroxymercuribenzoate. The *B.subtilis* enzyme may be harvested from a *B.subtilis* liquid culture by selective precipitation or other convenient techniques. For example, the culture can be centrifuged to remove cells and debris; brought to about 65% saturation with ammonium sulphate; recentrifuged to remove invertase and other protein contaminants and then brought to about 95% saturation with ammonium sulphate. Crude levansucrase is then precipitated, which can be further purified by being redissolved in phosphate buffer and dialysed.

The enzyme of choice is the fructosyltransferase obtained from *B.subtilis* NCIB 11871, although strains NCIB 11872 and 11873 are also of interest. The enzyme from these strains also has a broader specificity and can thus be more easily used with a range of 6-substituted derivatives.

According to a further feature of the present invention, there is provided a fructosyltransferase having a $K_m$ to sucrose of at least 0.1M in the absence of an acceptor aldose; which does not form significant amounts of alcohol-precipitable material from a fructose donor in the absence of an acceptor aldose; and which is unaffected by the presence of surfactants, has an optimum activity at about 30° C. and is active for at least 20 minutes at up to 45° C.

The two constants (K) cited with reference to these enzymes are $K_m$, the Michaelis-Menton constant, which is the substrate concentration at which half the maximum rate of enzyme reaction (to produce levan etc) occurs; and $K_i$, the inhibitor constant, which is the concentration of inhibitor which produces half the maximum observable inhibition of enzyme activity (to produce levan).

The $K_m$ for the strain NCIB 11871 enzyme is about 0.2M for sucrose in the absence of an acceptor, while the $K_m$ reported for Dedonder's levan sucrase from "*B.subtilis* BS5", (a clone from *B.subtilis* var. nigra) was only 0.02M.

*B.subtilis* NCIB 11871, and also strains NCIB 11872 and 11873, are atypical strains of *B.subtilis*. That is to say they meet nearly all the requirements of the species identification, both in classical tests (Berkley and Goodfellow, "The Aerobic Endospore-forming Bacteria: Classification and Identification" (1981) Academic Press, London; Gordon, Haynes and Pang, "The Genus Bacillus", Agriculture Handbook No.427 (1973) U.S. Dept of Agriculture, Washington D.C.) and in the API 50 CHB and API 20E systems (API system S.A, La Balme les Groltes—38390 Montalieu Vercieu, France and see Logan et al. J.Appl. Bact. 1978 pp 28–29). In these tests, the main significant difference from the majority of *B.subtilis* strains is that strain NCIB 11871 is a lactose-negative strain showing variable acid production from xylose. Strain NCIB 11872 is lactose negative and also gives negative results with D-mannose, melibiose and trehalose and in the ONPG reaction. Strain NCIB 11873 is lactose positive giving negative results with D-mannose and inulin.

The fructosyltransferase derived from many strains of *B.subtilis* and Erwina sp are generally regarded as being levansucrases: that is to say that in the presence of sucrose, they cause the production of levan, a polyfructose material which is alcohol precipitable. When they are used in the production of fructose disaccharides, the competing reaction to produce levan must be suppressed if any useful product is to be obtained, hence the restriction of these enzymes in GB No. 2046757A to reaction mixture containing high proportions of the acceptor molecule. However the *B.subtilis* NCIB 11871, 11872 and 11873 enzymes used here are much less prone to produce levan. The $K_m$ for sucrose for 'levan' production is about 0.2M. This compares with a quoted $K_m$ of about 0.02M for the Dedonder (loc.cit.) BS5 strain enzyme. Even when equivalent concentrations of the acceptor and donor molecules are used and when the conditions are used which were found to promote the synthesis of high molecular weight levan by the Tanaka *B.subtilis* enzyme (i.e. addition of levan primer, use of a low ionic strength solution, and reaction at low temperatures (J.Biochem 90, 521, 1981) very little high molecular weight levan is produced. Only after the peak yield of disaccharide is reached is a polymer of intermediate molecular weight formed. Furthermore, unlike other true levansucrases, the enzyme from *B.subtilis* NCIB 11871 appears not to catalyse a disproportionation reaction i.e. it does not convert low molecular weight oligosaccharides into high molecular weight levan. For instance trisaccharide can be detected, which should not be present if the enzyme carries out the disproportionation reaction. Standard levan obtained from *Aerobacter levanicum* (Sigma) can be fractionated into two peaks corresponding to high and intermediate molecular weight material. The Dedonder (loc.cit.) enzyme has an equilibrium constant (levan and glucose/sucrose) of about $3.6 \times 10^{-2}$ at 37° C., levan of DP40 being formed. In complete contrast, strains NCIB 11871, 11872 and 11873 produce an enzyme which produces no significant amount of alcohol-precipitable polysaccharide from sucrose alone, and even the growing cells of strain 11871 produce no levan. It thus appears that the fructosyltransferase produced is not effectively a 'levan sucrase' at all. In this specification it will be referred to as a fructosyltransferase.

The fructose source for the reaction may be any oligo- or di-saccharide containing a preferably unsubstituted β-fructosyl ring attached to the anomeric carbon of an aldose by a (1→2) link as in sucrose (β-D-fructofuranosyl α-D-glucopyranoside), raffinose (O-α-D-galactopyranosyl-(1→6)-O-α-D-glucopyranosyl-(1→2)β-D-fructofuranoside) or stachyose.

The 6-substituted aldose starting material of formula II may carry as a protected hydroxy group any substituent of the 6-position which is resistant to the subsequent chlorination reaction and which can be easily removed to release a 6-hydroxy group. 6-Carboxylic esters are preferred, e.g. the 6-acetate or benzoate. Glucose 6-acetate can be easily prepared by a variety of processes (e.g. Duff, J. Chem. Soc. p 4730-4 1957; Reeve et al J. Amer. Chem. Soc., 79,6041-3; Frohwein et al Nature p 153,1960; Duff et al. Nature p 103, 1957; ibid Biochem J.515–520, 70, 1958).

The 6-substituent of the aldose starting material of formula II may also be an ether, such as the benzyl ether which can be easily removed by hydrogenation or an aliphatic ether which can remain to provide a chlorinated 6-ether as disclosed in GB No. 2127806A. The starting material may also carry, for example, a 4-chloro substituent, to give a disaccharide already partially chlorinated, e.g. 4-chloro-4-deoxy-galactose 6-acetate.

The reaction between the fructose donor and the fructose acceptor should take place in an aqueous medium, preferably buffered at the optimal pH of the enzyme, i.e. at pH 5.4–6.0 at the optimum temperature of about 30° C. The two reactants are generally water soluble and the enzyme may be dispersed in the mutual solution or, preferably, immobilized on an insoluble support. Immobilization may, for example, be effected using an ion exchange resin such as DEAE cellulose, to which the enzyme is strongly adsorbed. Many other immobilization supports may be used, for instance bone char as disclosed in U.S. Pat. No. 4,421,850.

The ratio of fructose donor to fructose acceptor in the reaction mixture is of importance; too low and the yield is reduced; too high any possible levan reaction may not be suppressed particularly if a substrate of high solids content is used. In general, we find that a molar ratio (donor-acceptor) of about 2:1 is optimal. The reaction can be effected at fairly high concentration as there is no problem of solubility or viscosity. Typically, a reactant concentration of about 40% by weight is successful although higher concentrations may be used, depending on the solubility of the reactants, e.g. up to about 75% for glucose 6-acetate. The enzyme concentration must naturally depend on the activity, but levels of about 50 ml/liter have been successful when using an aqueous solution containing the enzyme derived from 33 ml of $B.subtilis$ NCIB 11871 culture per ml of solution.

The subsequent chlorination of a compound of formula III may be effected by use of any reagent capable of displacing hydroxy by chlorine selectively in the 4,1'- and 6'-positions. A reagent of choice is the Vilsmeier reagent, obtained by reacting a dialkylamide with a chlorinating reagent, e.g. dimethylformamide with phosphorus pentachloride, phosgene or thionyl chloride. A detailed description of the chlorination of sucrose 6-esters is given in GB No. 2079749A and U.S. Pat. No. 4,380,476. Similarly, the deprotection of a 6-ester is disclosed in the same publication, using for example sodium methoxide in methanol. A 6-benzyl ether group may be removed by hydrogenation.

There is further provided a method of preparing a fructoside by reacting a fructose-acceptor alcohol (especially an aldose) with a fructosyl di- or oligo-saccharide in the presence of a fructosyltransferase having a $K_m$ to sucrose of at least 0.1M in the absence of an acceptor aldose; which does not form significant amounts of alcohol-precipitable material from a fructose donor in the absence of an acceptor aldose; and which is unaffected by the presence of surfactants, has an optimum activity at about 30° C. and is active for at least 20 minutes at up to 45° C. The fructose acceptor may, in general be any pyranose or furanose sugar or substituted sugar which it is desired to incorporate in a fructosyl disaccharide. Examples include 6-substituted glucose derivatives, such as glucose 6-esters and ethers and 6-deoxy-D-glucose, (in the preparation of TGS and its sweet analogues), or any of the materials suggested for use with a levansucrase in U.K. Patent Application GB No. 2046757A (but see below). The fructosyl di- or oligo-saccharide may comprise sucrose, raffinose, or stachyose.

The substrate specificity of the enzyme from $B.subtilis$ 11871 is now described in more detail. Earlier studies showed that fructosyltransferase activity of $B.subtilis$ (Marburg) is not impaired by alterations at the C-6 of the aldose unless a polar group, such as phosphate, or a carboxylic acid group, is substituted into that position. In particular, it has been reported that the following alterations at the C-6 position of the acceptor do not inhibit levansucrase: reduction (L-galactose to L-fucose); replacement of OH by O-glucosyl (D-glucose to isomaltose); and hydroxyalkyl for H on C (D-galactose to D-glycero-D-galactoheptose) (Hestrin et al, 1958). Only molecules having a non-substituted fructose group linked to an alkosyl group by the same glycosidic bond as in sucrose may act as a donor, thus sucrose 6-acetate can act as the fructose donor instead of sucrose or raffinose.

However, in the case of the novel enzyme of this invention, a very wide range of sugars act to varying extents as acceptors for the fructose from sucrose or raffinose. Most of the acceptors are hexoses or pentoses such as ribose, sorbose, lyxose, arabinose and xylose. The only pentose known not to react is xylulose. Most of the reactive acceptors can adapt a pyranose ring configuration although xylitol and gluconic acid also appear to react. When a ring structure is present it must contain oxygen or sulphur, thus inositol does not react but 5-thioglucose does react.

All the variations in structure at carbons 3 and 4, e.g. galactose, 3-O-methylglucose, 4-chlorogalactose and D-arabinose instead of glucose, do not affect qualitative reactivity. Substituents at carbon 1, such as in methyl α-D-glucopyranoside, 1-thioglucose and sorbose, allow reaction. At carbon 2 a variety of changes are tolerated, e.g. as in mannose, but 2-deoxyglucose and glucosamine are unreactive. At carbon 6 most structural variations are tolerated such as the 6-phosphate, chloride and acetate, 6-deoxyglucose, 6-O-methylglucose and 6-O-methylgalactose and the 6-H as in rhamnose, but the $CH_2OH.CHOH-$ group of glucoheptose prevents reactivity.

Many of the disaccharides, including mellibiose, lactose, isomaltose, and cellobiose, are reactive acceptors, although certain disaccharides such as lactulose and isomaltulose are unreactive. When oligosaccharide acceptors are used, the acceptor activity decreases with increasing size, as in the homologous series maltose, maltotriose, maltotetraose etc.

Lastly, in many cases structural alterations (of glucose) at more than one carbon atom do not prevent reaction, e.g. galactose 6-acetate; and when mixtures of reactive acceptor molecules are used e.g. in hydrolysed whey, mixtures of fructosylated disaccharides are formed.

The following sugars are found to act as acceptors. D-arabinose, fucose, 6-deoxyglucose, 6-O-methylgalactose, lactose, galactose 6-acetate, mannose, 5-thio-D-glucose, maltose, 1-thio-glucose, maltotriose, 3-O-methyl α-D-glucose, maltopentaose, D(−)arabinose, maltohexose, 6-chloro 6-deoxyglucose, mellibiose, galactose, xylose, isomaltose, L-arabinose, whey permeate (lactose), 4-chlorogalactose, ribose, lyxose, glucose 6-acetate, gluconic acid, glucose 6-phosphate, L-rhamnose, 6-O-methylglucose, methyl-D-glucoside, xylitol, glycerol and ethanol.

One particularly interesting acceptor is xylose, leading to the production of β-D-fructofuranosyl (2→1) α-D-xylopyranoside, known as xylsucrose. Another interesting acceptor is galactose, leading to the production of β-D-fructofuranosyl (2→1)-D-galactopyranoside (galactosucrose). Products of this type are low in cariogenicity and/or sweetness, making them of interest as sucrose replacements in areas where excess sweetness is a problem. Galactosucrose is interesting particularly because it can be produced from, say, molasses and hydrolysed whey permeate, both readily available sources. It has only a trace of sweetness (ca. 10–15% of sucrose).

As regards donor specificity, sugars based on sucrose with an $\alpha(1\rightarrow2)$ bond as an absolute requirement are reactive, activity decreasing with the size of the molecule. The novel disaccharides formed by the action of the enzyme also act as donors, e.g xylsucrose.

The product of the enzyme-catalysed reaction can be separated from the by-products and starting materials by conventional physiochemical means such as chromatography especially high pressure liquid chromatography (HPLC) and ion-exchange resin chromatography. In particular, products having no 6-hydroxy group in the aldose ring, for example sucrose 6-esters and ethers, xylose-derived products and 6-deoxy sucrose, have a surprisingly low polarity which makes ion-exchange resin chromatography an easy and effective separation method. Polystyrene resins, cross-linked with divinyl benzene, e.g. the Amberlite XAD resins, are particularly suitable. This separation is much easier than the separation of variously substituted sucrose derivatives necessary when the sucrose 6-derivative is prepared by a chemical process.

The by-product of the fructose transfer reaction using a glucosyl fructoside such as sucrose, is glucose itself. Glucose is, of course, a potent acceptor, and competes with the desired acceptor, leading to re-fermation of the starting material. Removal of the glucose by conversion into fructose can therefore be desirable. This may be achieved by addition of glucose isomerase.

The following Examples illustrate the invention further:

EXAMPLE 1

Preparation of TGS (a) Preparation of enzyme

β-Fructosyltransferase was obtained from *Bacillus subtilis* strain NCIB 11871. The enzyme was induced by sucrose during growth of the cells on shake flasks (250 ml capacity, 4 flasks) containing minimal sucrose medium (100 ml per flask). The culture was incubated until the late exponential phase, shaking at 30° C., and the contents of the four shake flasks were then combined and the growth medium separated from the cells by centrifugation (5,000 g for 15 minutes). 20–30% of the total enzyme remained associated with the cells. The resulting supernatant was brought to sixty five percent saturation by the addition of solid ammonium sulphate and left to stand for 45 minutes at 0° C. This procedure precipitated most of the unwanted invertase and other protein contaminants but left the majority of enzyme in solution. The sample was then recentrifuged (20,000 g for 30 minutes) and the precipitate containing the invertase activity was discarded. More ammonium sulphate was added to the solution to bring the solution to ninety five percent saturation and left to stand for a further forty five minutes at 0° C. A second precipitate, primarily fructosyltransferase, was formed and was collected by centrifugation (40,000 g for 45 minutes) and redissolved in 12 ml 50 mM phosphate buffer, pH6.0. The net effect of the two precipitations and the resolubilisation of the second precipitate was a substantial purification and concentration of enzyme such that only one protein band could be detected by polyacrylamide gel electrophoresis. Finally, residual ammonium sulphate was removed from the enzyme preparation by dialysis (0° C. for 4 hrs) against the 50 mM phosphate buffer.

The dialysed enzyme was assayed before and after the addition of p-hydroxymercuribenzoate which inhibits invertase but does not affect fructosyltransferase activity. By this means the fructosyltransferase preparations were usually found to be free from invertase. The protein content of the preparations was estimated at 0.45 mg/ml by measuring their absorbance at 280 nm. A black pigment is often present even in the purified enzyme preparations but does not affect the activity of the preparations.

(b) Sucrose 6-acetate

Glucose 6-acetate (80 g dried in vacuo to constant weight) and granulated sucrose (160 g) were dissolved at room temperature in 100 ml of McIllvaine buffer at pH 5.4 and diluted to 600 ml (i.e. 40% w/v) with deionised water. This solution was then extensively filtered and 28 ml of the enzyme solution added. The reaction mixture was then incubated at 30° C. and sampled at time intervals until HPLC analysis showed that no further sucrose 6-acetate was being formed, the maximum concentration of sucrose 6-acetate reached being about 120 gl$^{-1}$. The enzyme was removed by filtering the reaction mixture through a column of DEAE cellulose which adsorbs the enzyme. Alternatively it could be denatured by heating at 65° C. for 1 hour. Removal of the enzyme is important as it may also catalyse the slow hydrolysis of the sucrose 6-acetate to release fructose.

The product was then isolated by preparative HPLC to give sucrose 6-acetate of at least 85% purity with an overall yield of about 50%. The initial rate of the enzyme reaction was to produce 244.5 mg sucrose 6-acetate per mg of enzyme per hour. The yield of the enzymic step was 58% based on glucose 6-acetate consumption or 48% based on sucrose 6-acetate formation.

(c) Chlorination of sucrose 6-acetate (i) Preparation of Vilsmeier reagent

Phosphorus pentachloride (140 g) was added to dry dimethylformamide (250 ml) in a beaker with vigorous stirring, the temperature being maintained at 70°–80° C. stirring was continued for 1 hour and the reaction was then cooled and filtered. The crystalline product was washed with dmf (2×20 ml) and diethyl ether (40 ml) and dried in a desiccator to give the Vilsmeier reagent as white crystals (93 g)

(ii) Preparation of sucrose 6-acetate solution:

Sucrose 6-acetate syrup (41 g, actual sucrose 6-acetate content 28 g) was dissolved in dmf and diluted to 86 ml. The solution was dried over molecular sieve and filtered.

(iii) Chlorination

Vilsmeier reagent (31 g) was added to dmf (80 ml) and the mixture was cooled to 0° C. Sucrose 6-acetate solution (21 ml, 7 g of sucrose 6-acetate) was added slowly, the temperature being maintained below 20° C. The reaction was stirred at 0° for 15 minutes, then transferred to an oil bath at 60° for 30 minutes. The bath was heated to 120° over 30 minutes and held at this temperature for 2 hours. The reaction was then cooled to 20° and neutralised by addition of methanol—880 ammonia (2:1, 80 ml), keeping the temperature below 50°. The reaction was concentrated to a syrup and acetylated by addition of pyridine (100 ml) and acetic anhydride (100 ml). After stirring at 50° for 2 hours, the reaction was cooled to 20° C. and methanol (80 ml) was added while maintaining the temperature below 60°. The reaction was then evaporated to a syrup and extracted with hot (60°) toluene (4×100 ml). The toluene extracts were concentrated to a syrup and dissolved in ethyl acetate (100 ml). The ethyl acetate solution was washed with water (3×100 ml) and the water was back extracted with ethyl acetate (2×50 ml). The combined ethyl acetate extracts were dried over magnesium sulphate, decolourised with activated charcoal and concentrated to a syrup which crystallised from industrial methylated spirit to give 4,1',6'-trichloro-4,1',6'-trideoxygalactosucrose pentaacetate (4.4 g, 39%).

(iv) De-esterification

The pentaacetate was dissolved in dry methanol and treated with a catalytic amount of sodium methoxide at room temperature for 5 hours. The solution was then deionised and evaporated to yield 4,1',6'-trichloro-4,1',6'-trideoxygalactosucrose (90%).

EXAMPLE 2

Preparation of 4,1',6'-trichloro-4,6,1',6'-tetradeoxygalactosucrose (6-deoxy-TGS) (an analogue of TGS having a similar degree of sweetness)

(1) 6-Deoxysucrose

Isolation, purification and crystallisation

6-Deoxy-D-glucose (D-quinovose, 20 g) and sucrose were subjected to a reaction similar to that in Example 1, yielding a mixture of 6-deoxysucrose, D-quinovose, sucrose and glucose, total volume 140 ml. The 6-deoxysucrose was separated from the mixture by preparative hplc, using a Waters Prepak 500-C18 reverse-phase column and water as eluant. A surprisingly large difference in retention time was observed between that of 6-deoxysucrose and those of the other components in the mixture. D-Quinovose, sucrose and D-glucose were eluted 4–9 min after injection and 6-deoxysucrose only after 29 min (max.peak height). The large separation interval allows more material to be separated per injection than would otherwise be possible. Eluant containing 6-deoxysucrose was evaporated to dryness under reduced pressure (bath temperature 50° C.) to yield a clear syrup (16.7 g, 42%) which crystallised on standing at room temperature. The product was recrystallised from ethanol and had m.p. 180°–181° C., $[\alpha]_D+57.6°$ (c 2.5, water); mass spectrum, m/e 293 (M+—CH$_3$—H$_2$O); $^{13}$C-NMR spectrum (D$_2$O solution, relative to internal DSS at 0 ppm):

| Carbon atom | Chemical shift, ppm |
| --- | --- |
| 2' | 106.32 |
| 1 | 94.70 |
| 5' | 84.01 |
| 3' | 79.04 |
| 5 | 77.74 |
| 4' | 76.73 |
| 3 | 74.93 |
| 2 | 73.95 |
| 4 | 71.09 |
| 6' | 65.02 |
| 1' | 63.77 |
| 6 | 19.36 |

(2) Selective chlorination of 6-deoxysucrose

6-Deoxysucrose (2.8 g) was dissolved in DMF (10 ml) and the solution added to a suspension of Vilsmeier reagent (15 g) in DMF (30 ml), keeping the temperature below 10° C. The mixture was stirred at room temperature for 10 min and then heated to 120° C. for 2 h with stirring. The reaction was cooled to room temperature and methanol-ammonium hydroxide solution (1:1, 20 ml) added. The mixture was concentrated at 70° C. and toluene (2×20 ml) was evaporated from the residue which was then acetylated with acetic anhydride (30 ml) in pyridine (30 ml) at 60° C. for 3 h. Methanol (50 ml) was added and the mixture evaporated to a residue which was extracted with toluene at 60° C. (4×50 ml) by stirring and decantation. The combined toluene extracts were evaporated to dryness and the residue chromatographed on silica gel (petroleum ether-ether, 2:1, then 1:1 as eluant) to yield the intermediate 4,1',6'-trichloro-4,6,1',6'-tetradeoxygalactosucrose tetraacetate as a pale yellow syrup after evaporation of solvents (3.1 g, 64%); mass spectrum, m/e 283,285,287 (9:6:1, dichloro-di-O-acetylfructose residue) and peaks corresponding to successive loss of 60 (CH$_3$CO$_2$H), 42 (CH$_2$=C=O) and 36 (HCl); 249,251 (3:1,-monochlorodideoxy-di-O-acetyl galactose residue with loss of CH$_2$) and peaks corresponding to successive loss of 60 and 42.

The tetraacetate was dissolved in methanol (30 ml) and deacetylated with sodium methoxide (1M, at pH 9) at room temperature. The solution was neutralised with Amberlyst 15 (H+) cation-exchange resin, filtered and evaporated to dryness. The product was obtained as a white solid, $[\alpha]_D+87.1°$ (c 1.0, acetone); $^{13}$C-NMR spectrum (D$_2$O solution, relative to internal DSS at 0ppm):

| Carbon atom | Chemical shift, ppm |
| --- | --- |
| 2' | 106.02 |
| 1 | 95.41 |
| 5' | 83.75 |
| 3' | 78.89 |
| 4' | 78.04 |
| 5 | 70.95 |
| 4 | 70.03 |
| 2 | 69.78 |
| 3 | 69.28 |
| 1' | 47.46 |
| 6' | 45.99 |
| 6 | 19.61 |

4,1',6'-Trichloro-4,6,1',6'-tetradeoxygalactosucrose was found to be 400 times as sweet as sucrose (8% solution).

EXAMPLE 3

The process of Example 1 was repeated, but using glucose 6-benzoate instead of the 6-acetate in stage (b). A similar result was obtained and stage (c) was effected as before to produce TGS in similar yield.

EXAMPLE 4

The process of Example 1 can be modified by using an enzyme derived from the B. subtilis Marburg strain 168, strain NCIB 11872 or strain NCIB 11873 in stage (b). The reaction proceeds similarly, but at a lower reaction rate.

EXAMPLE 5

Immobilisation and Purification of fructosyltransferase from B. subtilis NICB 11871 using DEAE Ion-Exchange Cellulose and preparation of xylsucrose DEAE ion-exchange cellulose (DE 52) was washed exhaustively in 50 mM McIlvaine Buffer pH 5.4 and then with buffered substrate (sucrose-xylose 2:1, 40% w/v, total sugars). After filtering almost to dryness on a Buchner filter, the DEAE cellulose (10 g) was mixed with 8 ml of a fructosyltransferase preparation from *Bacillus subtilis* as in Example 1 for fifteen minutes at 30° C. with stirring. The resulting mixture of DEAE cellulose and enzyme was packed into a 10 ml jacketed column (19×1 cm) and maintained at 30° C. with a Churchill thermocirculator. The DEAE cellulose was allowed to drain under gravity and the drainings collected. A substrate was pumped up the column at a flow rate of about 1.0 ml h$^{-1}$ using a Watson-Marlow pump and eluant was collected at time intervals and assayed for fructosyltransferase activity. Adsorbance at 280 nm (OD$_{280}$) was also measured. To assay the sample, a 0.1 ml portion of the liquid sample or 0.1 g of immobilised enzyme (on DE 52) was incubated with 2 ml of substrate at 30° C. for 4 hours. Using a xylose/sucrose substrate for the preparation of "xylsucrose" the protein concentration and activity of the depleted solution remaining after the immobilization procedure had been terminated was compared with the protein concentration and activity of the original enzyme preparation. It was found that 68.5% of the enzyme originally present in the cell extract had been immobilized together with 83% of the protein originally present. The immobilized enzyme had an initial activity of 80.2% of that of an equivalent quantity of free enzyme; the activities of the two preparation being 0.38 g xylsucrose/g immobilized enzyme/h and 0.865 g xylsucrose/ml enzyme extract/h, respectively.

The immobilized enzyme (10 g w/w) was run continuously, packed into a column at 30° C., for about 2 weeks without any change in the pH of the eluate or evidence of microbial contamination. A little protein and enzyme was desorbed during the first three days of operation amounting to 24% of the protein initially adsorbed and 2.3% of the enzyme activity initially adsorbed. The immobilized enzyme activity decayed with an operational half-life of 95 h and showed the usual inverse relationship between the degree of conversion of substrates into products and flow rate through the column. At the slowest flow rate used, 0.086 empty column volumes per hour (ecv)h$^{-1}$, a 80% conversion into xylsucrose was achieved the column eluate containing 21 g l$^{-1}$ of xylsucrose. This yield was higher than any obtained in batch reactions probably because the plug-flow kinetics of the column favour the formation of xylsucrose since the products are continually being displaced out of the column and so do not accumulate and cause product inhibition. In total during these operations, some 20-25 g of xylsucrose was formed in a state from which pure xylsucrose can readily be obtained.

Unlike the soluble enzyme used initially, the immobilised enzyme led to some side products being formed during the reaction. A little fructose was formed, less than that produced by the original enzyme extract used for immobilization probably because the invertase activity which contaminates the extract was only partially adsorbed to the DE52. Several minor compounds which were eluted very late from the HPLC column, with retention times of 13 and 20 min, were observed in the eluate from the immobilized enzyme although they had never been noticed during analysis of the soluble enzyme reactions. These are probably oligosaccharides formed from the usual reactants by the enzyme. It is thought that the hold up of reactant molecules by the immobilized enzyme increases their contact time with the enzyme so that the possibility of polymerization occurs.

Since the xylose content of the substrate was 133 gl$^{-1}$, the maximum possible xylsucrose concentration was 266 gl$^{-1}$. The maximum concentration observed, at 0.086 ecvh$^{-1}$ was 80% of this, i.e. 210 gl$^{-1}$, but calculated on the basis of xylose consumed during the reaction, gives a 69.5% reaction. Yields are higher than in batch reactions because the 'flow-through' nature of the process causes product to be constantly removed and because the product is relatively non-polar compared with the substrates and so is selectively partitioned away from the positively charged immobilization support, both effects tending to favour the production of xylsucrose.

The same method was used to produce sucrose 6-acetate from glucose 6-acetate, 6-O-methyl sucrose from 6-O-methyl glucose, and 6-O-benzylsucrose from 6-O-benzylglucose.

The enzyme prepared according to Example 1 (0.1 ml) was mixed with 2 ml of a 40% w/v solution of sucrose and xylose (1:1), buffered at pH 5.5 at 30° C., and the reaction was monitored. Xylsucrose was estimated by HPLC. Levan formation was estimated optically. The results of a comparison with various enzymes were as follows:

| Source | g Xylsucrose/ml Enzyme per hour | Levan Formation |
|---|---|---|
| NCIB 11871 | 8.6 | 0 |
| NCIB 11872 | 2.9 | DETECTABLE |
| NCIB 11873 | 1.4 | + |
| NCIB 3610 (MARBURG) | 0.08 | ++ |
| FERM 3119/1979 (*B. Subtilis* Var. *Sacchardarolyticus* | 0.19 | ++ |
| NCIB 9966 (*Erwinia herbicola*) | 0.87 | ++ |

Thus enzymes according to the invention produce at least 10 times more xylsucrose than the Marburg strain enzyme: at least 100 times more in the case of the NCIB 11871 enzyme. The competing production of levan is much less.

EXAMPLE 6

Preparation of galactosucrose 15 ml of a 40% (w/v) substrate containing equal weights of sucrose and galactose dissolved in phosphate-citrate buffer (pH 5.9) was incubated at 30° C. with a small volume of *Bacillus subtilis* NCIB 11871 fructosyltransferase partially purified by precipitating the enzyme with 95% sat. ammonium sulphate solution, redissolving the precipitate and precipitating impurities with 65% sat. ammonium sulphate solution.

After about 24 hours incubation, the products were separated by HPLC chromatography on a reverse-phase column (porous graphitic carbon, 5 micron diameter; eluant 5% aqueous acetonitrile). No further increase in the yield of galactosucrose could be obtained on further incubation or by adding fresh enzyme. Maximum yields of galactosucrose were about 0.33 g/g galactose and about 0.45 g/g sucrose consumed.

EXAMPLE 7

4,1',6'-Tribromo-4,1',6'-trideoxygalactosucrose (a) Preparation of Vilsmeier reagent Thionyl bromide (280 ml) was added to dried, cooled dimethylformamide (260 ml) with vigorous stirring. The mixture was stirred for 30 minutes at 70°-80° C. and then for a further hour and allowed to cool to ambient temperature. The mixture was filtered and the residue washed with dimethyl formamide (2×50 ml) and diethyl ether (100 ml) and dried in a desiccator, to yield 320 g reagent.

(b) Bromination of sucrose acetate

A solution of sucrose 6-acetate (5 g) in dmf (20 ml) was prepared as in Example 1 and was treated with a cooled suspension of the Vilsmeier reagent (25 g) in dmf (50 ml) with stirring, maintaining the temperature below 20° C. for 30 minutes. The stirred mixture was then stirred at ambient temperature for 30 minutes and then heated to 110° C. and stirred for a further 1.75 hours. It was then cooled to 20° C. and neutralised by addition of a 2:1 mixture of methanol and conc. (0.880) ammonia, maintaining the temperature below 40° C. The mixture was then concentrated to a syrup and acetylated with acetic anhydride (100 ml) in pyridine (100 ml) at 50° C. for 2 hours. The product was recovered as in Example 1 as the tribromogalactosucrose pentaacetate (4.2 g) identical with that in GB No. 2101989A. This was deacelylated with sodium methoxide (1 molar in methanol, at pH 9) at ambient temperature for 5 hours and then deionised with Amberlyst 15 (H+) ion-exchange resin. The supernatant was evaporated to dryness to yield the pure tribromo sugar, identical with that in GB 2101989A.

EXAMPLE 8

Chlorination of xylsucrose

Xylsucrose (from Example 5) (3 g) was dissolved in dmf (6 ml) at 10° C. and added with stirring to a cold suspension of the Vilsmeier reagent from Example 1 (13 g) in dmf (25 ml) maintaining the temperature below 10° C. The stirred mixture was then warmed to room temperature over 30 minutes and then to 120° and held with stirring for 3 hours. The mixture was then cooled, neutralised with 1:1 methanol/conc. (0.880) ammonia and concentrated at 70° C. Moisture was removed by successive toluene evaporations and then the residue was acetylated with acetic anhydride (30 ml) and pyridine (30 ml) at 60° C. for 3 hours. The mixture was then treated with methanol (50 ml) and evaporated to dryness. The residue was extracted with hot toluene (60° C. 4×50 ml) and the decanted extracts were combined and evaporated. The residue was chromatographed on silica gel (petroleum ether:diethyl ether 2:1, then 1:1) to yield the trichloro arabino sucrose tetracetate as a syrup (2.6 g).

Mass spectrum m/e 283,285,287 (9:6:1, dichloro-di-O-acetyl fructose residue); peaks corresponding to successive loss of 60 ($CH_3CO_2H$), 42 ($CH_2=C=O$) and 36 (HCl);

235,237 (3:1, monochloro-di-O-acetyl arabinos residue) and peaks corresponding to successive loss of 60 and 42.

The tetraacetate was dissolved in methanol (30 ml) and deacetylated with 1 molar sodium methoxide in methanol at pH 9, at ambient temperature.

The mixture was deionised with Amberlyst 15(H+) resin and filtered and evaporated. The product was isolated as a solid foam $[\alpha]_D$ 101.9° (c 1.1, Acetone); $^{13}C$-NMR spectrum $b_2$ relative to internal DSS at 0 ppm).

| Carbon atom | Chemical shift, p.p.m |
|---|---|
| 2' | 106.0 |
| 1 | 95.8 |
| 5' | 83.9 |
| 3' | 78.8 |
| 4' | 77.9 |
| 2 | 70.6 |
| 3 | 70.4 |
| 5 | 66.4 |
| 4 | 63.9 |
| 1' | 47.3 |
| 6' | 45.9 |

The compound was found to be 25 times as sweet as sucrose in a 2% solution.

We claim:

1. A process for the preparation of a halodeoxy sucrose of galactosucrose derivative of the formula

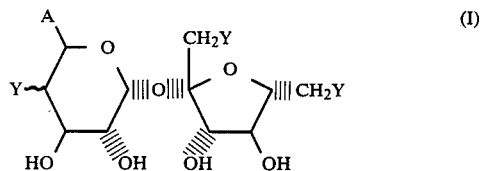

(I)

in which A represents a hydrogen atom or the group $CH_2X$, where X represents a hydrogen atom, or a hydroxy or alkoxy group and Y represents a halogen atom, comprising reaction of an aldose of the formula

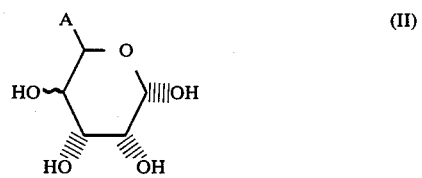

(II)

in which A represents a hydrogen atom or the group $CH_2X$, where X represents a hydrogen atom or an alkoxy group or a protected hydroxy group, with a fructosyldi or oligo-saccharide in the presence of a fructosyltransferase to obtain a compound of the general formula

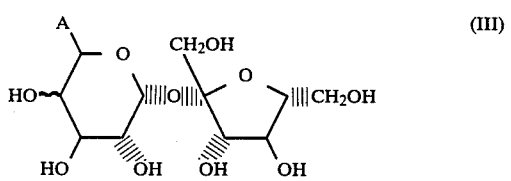

(III)

in which A is as defined for formula II, separating said compound of formula III; halogenating the compound of formula III and, for a compound of the formula I in which A represent $CH_2X$ and X represents a hydroxy group, de-protecting the protected hydroxy group wherein said fructosyltransferase is an enzyme isolated from bacteria which hydrolizes a donor fructosyl oligosaccharide or disaccharide containing an unsubstituted-fructosyl ring attached to the anomeric carbon atom of an aldose by a (1→2) linkage and transfers the fructosyl moiety so released to an acceptor aldose to yield a fructosyl disaccharide as the main product, said enzyme being capable of forming 6-substituted sucrose derivatives as the main product when the acceptor aldose is a 6-substituted glucose, said enzyme producing no significant amounts of alcohol precipitatable oligo- or polyfructoses in the absence of an aldose acceptor, said enzyme having a Km for sucrose of at least 0.1M in the absence of an aldose acceptor and being free from invertase activity, said enzyme being unaffected by the presence of surfactants, having an optimum activity at about 30° C. and being active for at least 20 minutes at up to 45° C.

2. A process according to claim 1, in which the frustosyltransferase is derived from B subtilis or Erwinia sp.

3. A process according to claim 2, in which the fructosyltransferase is derived from *B.subtilis* strain NCIB 11871, NCIB 11872 or NCIB 11173.

4. A process according to claim 1 in which the fructosyl saccharide is sucrose, raffinose or stachyose.

5. A process according to claim 1, in which chlorination is effected by use of a Vilsmeier reagent.

6. A process according to claim 1, in which the protected hydroxy group is an aliphatic or aromatic carbonyloxy group and is deprotected by hydrolysis; or is an arylalkoxy group and is deprotected by reductive cleavage.

7. An enzyme isolated from bacteria, which enzyme hydrolizes a donor fructosyl oligosaccharide or disaccharide containing an unsubstituted β-fructosyl ring attached to the anomeric carbon atom of an aldose by a (1→2) linkage and transfers the fructosyl moiety so released to an acceptor aldose to yield a fructosyl disaccharide as the main product, said enzyme being capable of forming 6-substituted sucrose derivatives as the main product when the acceptor aldose is a 6-substituted glucose, said enzyme producing no significant amounts of alcohol precipitatable oligo- or polyfructoses in the absence of an aldose acceptor, said enzyme having a Km for sucrose of at least 0.1M in the absence of an aldose acceptor and being free from invertase activity, said enzyme being unaffected by the presence of surfactants, having an optimum activity at about 30° C. and being active for at least 20 minutes at up to 45° C.

8. An enzyme according to claim 7 which has been treated with a selective invertase inhibitor.

9. An enzyme according to claim 8 in which the inhibitor is p-hydroxymecuribenzoate.

10. An immobilized enzyme according to claim 7.

11. An immobilized enzyme according to claim 10 immobilized on an ion exchange resin.

12. A fructosyltransferase according to claim 7, derived from *B.subtilis*.

13. A fructosyltransferase according to claim 12, derived from *B.subtilis* strains NCIB 11871, 11872 or 11873.

14. A process for the preparation of a fructoside from an alcohol by treating an aqueous solution of the alcohol and a fructosyl di- or oligosaccharide, with a fructosyltransferase according to claim 7, and separating the fructoside from the reaction mixture.

15. A process according to claim 1 or claim 14, in which the enzyme is immobilised.

16. A process according to claim 14, in which the alcohol is selected from: D-arabinose, L-fucose, 6-deoxyglucose, 6-O-methylgalactose, lactose, galactose 6-acetate, mannose, 5-thio-D-glucose, maltose, 1-thioglucose, maltotriose, 3-O-methyl α-D-glucose, maltopentaose, D-arabinose, maltohexaose, 6-chloro-6-deoxyglucose, mellibiose, galactose, xylose, isomaltose, L-arabinose, whey permeate (lactose), 4-chlorogalactose, ribose, lyxose, glucose 6-acetate, gluconic acid, glucose 6-phosphate, L-rhamnose, 6-O-methylglucose, methyl α-D-glucoside, xylitol, glycerol and ethanol.

17. A process according to claim 14 in which the fructosyl di- or oligo saccharide is selected from sucrose, raffinose, stachyose.

* * * * *